United States Patent [19]

Zampini

[11] Patent Number: Plant 6,962

[45] Date of Patent: Aug. 1, 1989

[54] *ILEX GLABRA* NAMED 'CHAMZIN'

[76] Inventor: James W. Zampini, P.O. Box 122, Perry, Ohio 44081

[21] Appl. No.: 243,149

[22] Filed: Sep. 9, 1988

Related U.S. Application Data

[63] Continuation of Ser. No. 127,629, Dec. 1, 1987, abandoned, which is a continuation of Ser. No. 30,288, Mar. 23, 1987, abandoned, which is a continuation of Ser. No. 787,691, Oct. 15, 1985, abandoned, which is a continuation of Ser. No. 697,271, Feb. 1, 1985, abandoned, which is a continuation of Ser. No. 551,719, Nov. 15, 1983, abandoned.

[51] Int. Cl.[4] ..... A01H 5/00
[52] U.S. Cl. ..... Plt./65
[58] Field of Search ..... Plt./65

[56] References Cited

PUBLICATIONS

Graves, A. H., *Illustrated Guide to Trees and Shrubs,* Pub: A. H. Graves, 1952, pp. 142 and 143.

Rehder, A., *Manual of Cultivated Trees and Shrubs,* Pub: The Macmillan Company, N.Y. 1960, p. 550.

Wyman, W., *Shrubs and Vines for American Gardens,* Macmillan Pub. Co., Inc., New York, 1973, pp. 256, 257.

Hillier, H. G., *Hilliers Manual of Trees and Shrubs,* Pub. A. S. Barnes and Company (1979) p. 158.

*Primary Examiner*—James R. Feyrer

*Attorney, Agent, or Firm*—Watts, Hoffmann, Fisher & Heinke Co.

[57] ABSTRACT

The present invention relates to a new and distinct variety of inkberry, which was discovered by me as a sport in a block of Ilex on my cultivated property, at Perry, Ohio. More particularly, the present invention relates to a novel variety of *glabra* compacta, *Ilex,* having unusual and distinctive characteristics, now available as Nordic, a trademarked plant of Lake County Nursery Exchange, Inc.

3 Drawing Sheets

RELATED APPLICATIONS

This application is a continuation of application Ser. No. 127,629, filed Dec. 1, 1987, which is a continuation application of application Ser. No. 030,288 filed 3/22/87 which is a continuation of application Ser. No. 787,691 filed 10/15/85 which is a continuation of application Ser. No. 697,271 filed 2/1/85 which is a continuation of application Ser. No. 551,719 filed 11/15/83, all abandoned.

TECHNICAL FIELD

The present invention relates to a new and district variety of inkberry, which was discovered by me as a sport of my cultivated property, at Perry, Ohio. More particularly, the present invention relates to a novel cultivar of *Ilex glabra* compacta having unusual and distinctive characteristics, which is identified by the varietal reference Chamzin of the Lake County Nursery, Inc., Perry, Ohio.

BACKGROUND OF THE PLANT

The *Ilex glabra* compacta is of the acuifoliaceae family. This plant generally produces a berry-like fruit (black drupe) from September until May of the following year. This plant has leaves which are obovate to oblanceolate in shape, 2 to 5 centimeters long and which are relatively thin compared to the *Ilex crenata* forms with which it is often confused. This plant generally has a habit which is upright and loose-branched so as to give the overall appearance of an erect-rounded evergreen shrub. This plant somewhat opens with age and upon losing the lower leaves therof. Previously, such plant has had a leaf color which is dark green and lustrous above in summer; sometimes becoming light yellow-green in summer.

DESCRIPTION OF THE PREFERRED PLANT VARIETY

Figure 7:
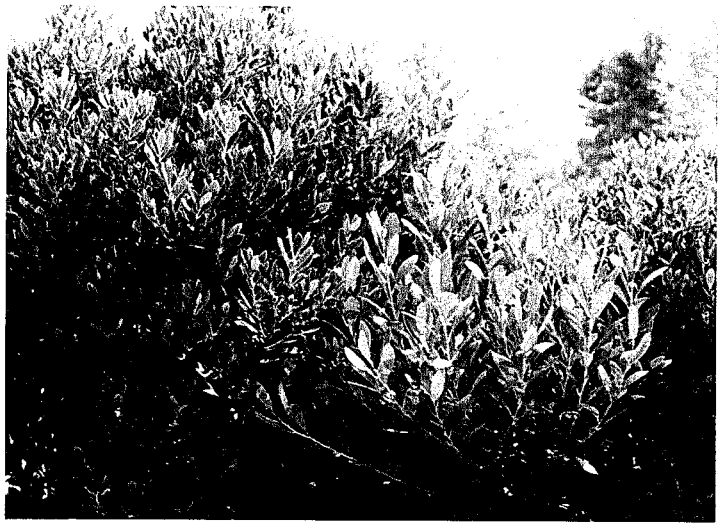
FIG. 7 is a side-by-side comparison of the *Ilex glabra* (left) with the Ilex plant of my invention (right) and showing a dense rounded, compact habit characterized by more spreading than upright growth habits.
Figure 8:
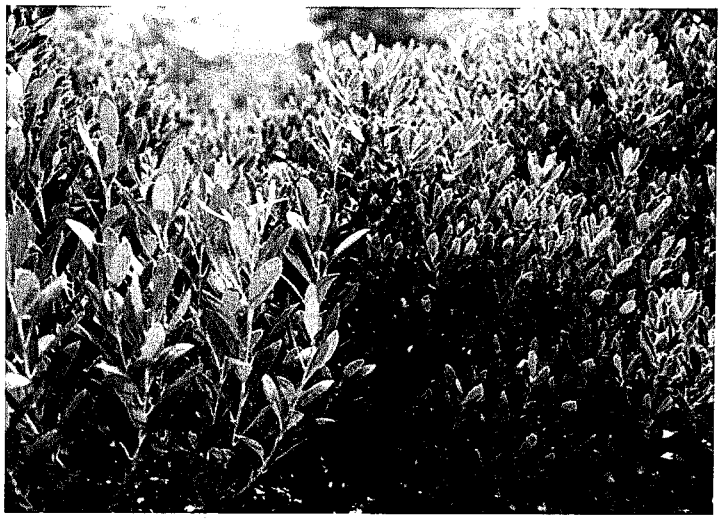
FIG. 8 is a side-by-side comparison of the *Ilex glabra* (right) with the Ilex plant of my invention (left) which shows such rounded, spreading and upright growth habit.

In this invention, my new Inkberry plant is a hardy holly with a dense rounded, compact habit. As contrasted with the *Ilex glabra* species in general, my new plant is much more vigorous and matures at about one-half the species' size under similar growing conditions. As contrasted with the compacta cultivar, my new plant exhibits a more spreading habit, as seen in FIGS. 7 and 8. My new plant is more spreading than upright, but the branches are upright which gives an overall rounded appearance to the plant. The plant is more dense at the base and at the center to provide a more compact habit and rounded habit compared to the *Ilex glabra*.

Figure 4:
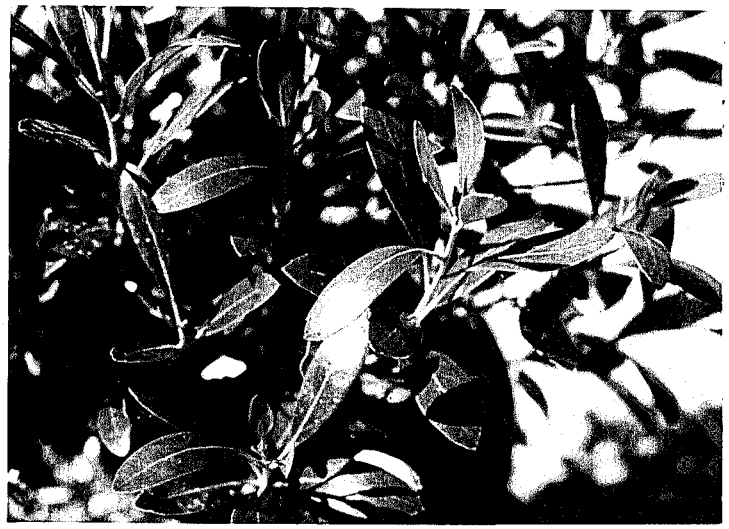
FIG. 4 shows the leaf of my new Ilex plant with the upper surface portion being of a dark-glossy-green color with such top surface having a substantially greater lustrous green color that glistens in the natural sunlight.
Figure 6:
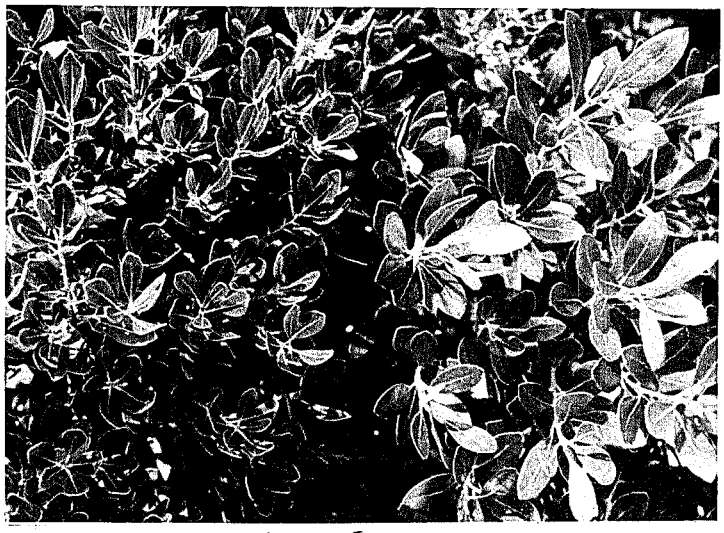
FIG. 6 is a side-by-side comparison of the *Ilex glabra* (left) plant leaves with the leaves of my new Ilex plant (right)

In general, the leaves of the new plant are of a dark lustrous green that glistens in the sunlight as if sprayed with a leaf polish, as seen in FIG. 4. Compared to the *Ilex glabra* compacta, the leaves are more heavily textured with a darker green foliage having a markedly more glassy (i.e. high luster) surface, as seen in FIGS. 4 and 6.

Asexual reproduction of my new inkberry plant was performed by me at Perry, Ohio, Zone 5, by taking soft wood cuttings which rooted and grew. The cuttings exhibited the same form and growth habit, and had leaves of the same shape, texture and glossiness as described above. Subsequent propagations exhibited identical growth and foliage patterns. Such reproduction shows that the forefoing characteristics and distinctions take place and are established and transmitted through succeeding propagations of the inkberry.

The following is a specific description by way of a specific example of such a new inkberry cultivar, color terminology being referenced to the Munsell Book of Color, Baltimore, Md., 1950, hereinafter referred to as Munsell.

Leaves: The leaves have a coriaceous surface appearance with an alternate, obovate to oblanceolate configuration. The leaves have a length of between about two to five centimeters and a width of about between one-third to one-fourth centimeter with one to three teeth on each side near the apex. The glabrous and punctate leaves are of a dark-glossy-green (Munsell GYG $\frac{3}{4}$) above and a light dullish green (Munsell GY 5/4) color below, as seen in FIGS. 4 and 5.

Shrub: The plant at maturity may have a height of between about 120 to 150 centimeters with the spread being between 150 to 180 centimeters giving the overall appearance of the plant being more spreading than upright.

Flowers: The flowers are similar to the Ilex crenata forms.

Figure 1:
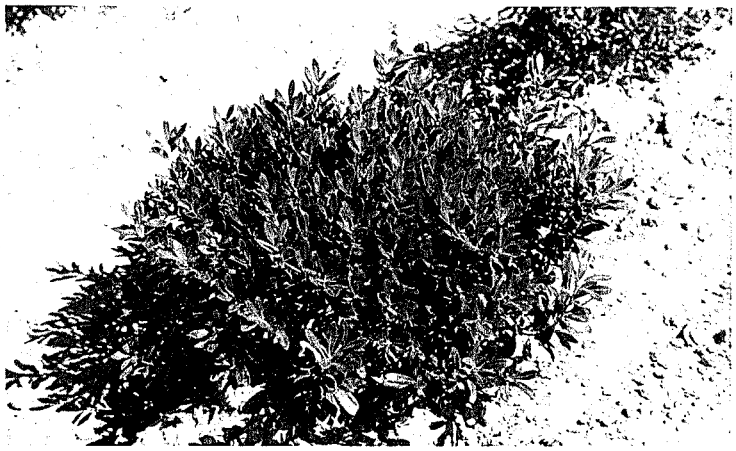
FIG. 1 shows my new Ilex plant in the summer growing season.
Figure 2:
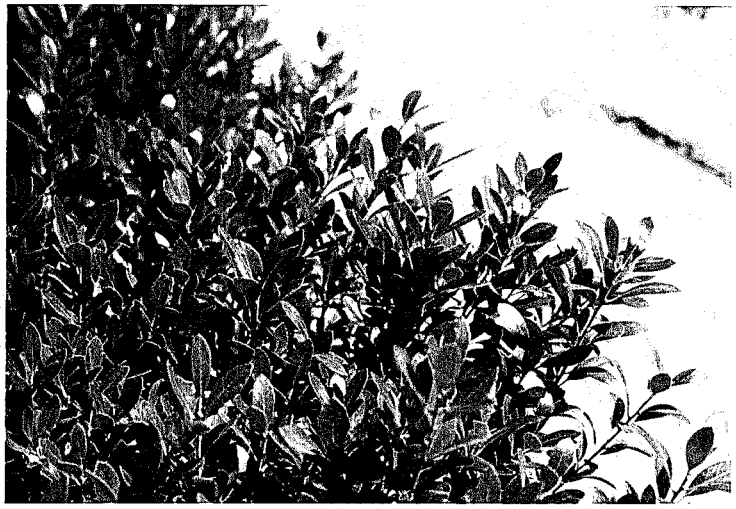
FIG. 2 illustrates a closer view of a portion of the branches of the plant illustrated in FIG. 1.
Figure 3:
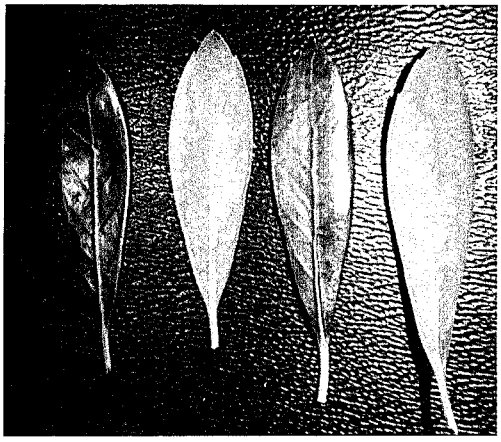
FIG. 3 illustrates a random sample of four leaves removed from the plant for purposes of clarity showing upper and lower leaf surfaces.
Figure 5:
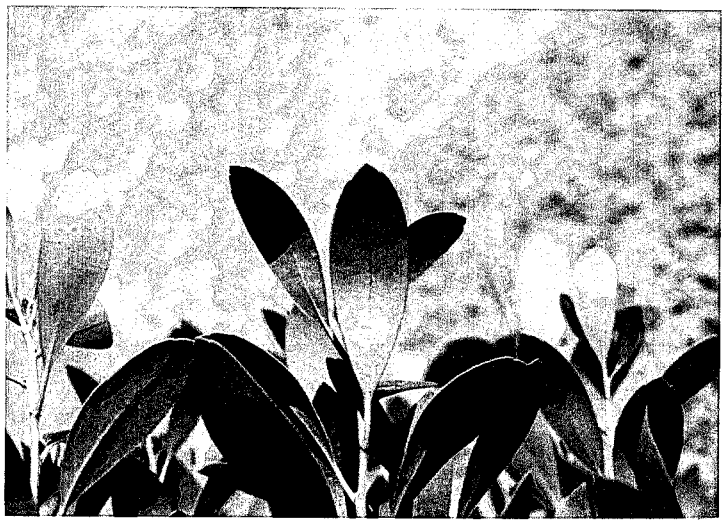
FIG. 5 shows the leaf of my new Ilex plant with the lower surface being of a light dull-green color.

The characteristics of my new plant which distinguishes it from *Ilex glabra* and *Ilex glabra* compacta is high glossy luster or sheen on the top or upper surface of the leaf contrasting with the dull appearing green color on the back or inner side of the leaf, as best shown in FIGS. 3, 4 and 5.

A further and important distinguishing characteristic of the present plant variety is that it is an exceptionally hardy plant which takes trimming readily and hence, can be easily maintained in the landscape. This plant variety exhibits vigorous growth habits compared to similar Ilex species.

I claim:

1. A new and distinct cultivar of *Ilex glabra* plant, substantially as herein shown and described, characterized particularly by a more spreading than upright growth and which is more compact at the center and base to provide a well branched and more rounded habit, the plant has a more vigorous growth and matures at about one-half the species size under such growing conditions, and having leaves which are of a dark-glossy-green color above and of a light dull-green color below, and with the top surface of the leaves having a substantially greater lustrous green color that glistens in natural sunlight.

* * * * *

UNITED STATES PATENT AND TRADEMARK OFFICE

CERTIFICATE OF CORRECTION

PATENT NO. : PPO 6,962

DATED : August 1, 1989

INVENTOR(S) : James W. Zampini

It is certified that error appears in the above-identified patent and that said Letters Patent is hereby corrected as shown below:

In the Abstract, line 7, change "Nordic" to -- Chamzin --.

Signed and Sealed this

Thirty-first Day of August, 1993

Bruce Lehman

*Attest:*

BRUCE LEHMAN

*Attesting Officer*

*Commissioner of Patents and Trademarks*